United States Patent [19]

Poss et al.

[11] Patent Number: 5,350,752
[45] Date of Patent: Sep. 27, 1994

[54] DIHYDROPYRIMIDINE DERIVATIVES
[75] Inventors: Michael A. Poss, Lawrenceville, N.J.; John Lloyd, Yardley; Karnail S. Atwal, Newtown, both of Pa.
[73] Assignee: E. R. Squibb & Sons, Inc., Princeton, N.J.
[21] Appl. No.: 812,235
[22] Filed: Dec. 16, 1991
[51] Int. Cl.⁵ .................. C07D 239/90; C07D 239/93; C07D 257/09; A61K 37/505
[52] U.S. Cl. .................. 514/259; 544/284; 544/287; 544/231; 544/244
[58] Field of Search .............. 544/284, 287, 231, 244; 514/259

[56] References Cited

U.S. PATENT DOCUMENTS

| | | | |
|---|---|---|---|
| 4,820,843 | 4/1989 | Aldrich et al. | 548/252 |
| 4,855,301 | 8/1989 | Atwal et al. | 514/269 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 5,037,829 | 8/1991 | Freyne et al. | 514/259 |
| 5,162,325 | 11/1992 | Chakravarty et al. | 514/259 |
| 5,162,326 | 11/1992 | Naka et al. | 514/269 |

FOREIGN PATENT DOCUMENTS

| | | |
|---|---|---|
| 253310 | 1/1988 | European Pat. Off. . |
| 323841 | 7/1989 | European Pat. Off. . |
| 324377 | 7/1989 | European Pat. Off. . |
| 411766 | 2/1991 | European Pat. Off. . |
| 0445811A2 | 9/1991 | European Pat. Off. . |

OTHER PUBLICATIONS

Karnail S. Atwal et al., "Substituted 1,4-Dihydropyrimidines, 3, Synthesis of Selectively Functionalized 2-Hetero-1,4 dihydropyrimidines", J. Org. Chem., (1989), 54, pp. 5898–5907.
Peter Bühlmayer et al., "Nonpeptidic Angiotensin II Antagonists: Synthesis and in Vitro Activity of a Series of Novel Naphthalene and Tetrahydronaphthalene Derivatives", J. Med. Chem., (1991), 34, pp. 3105–3114.
Chiu et al., European Journal of Pharmacology, 157 (1988) pp. 13–21.

Primary Examiner—Mukund J. Shah
Assistant Examiner—Matthew V. Grumbling
Attorney, Agent, or Firm—Ellen K. Park

[57] ABSTRACT

Novel A-II receptor antagonists have the formula

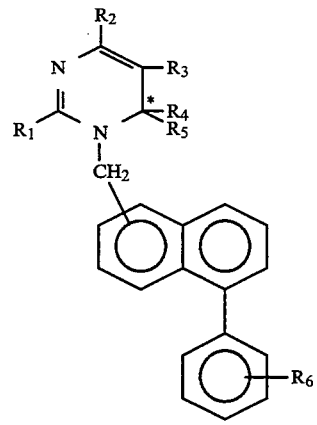

or its isomer

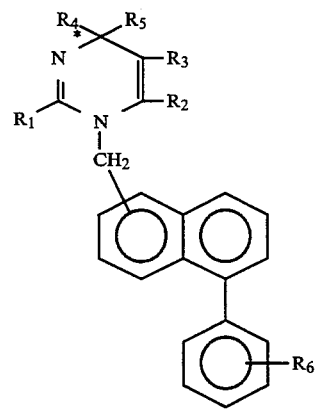

wherein $R_1$, $R_2$, $R_3$, $R_4$, $R_5$, and $R_6$, are as defined herein. These compounds inhibit the action of angiotensin II and are useful, therefore, for example, as antihypertensive agents.

7 Claims, No Drawings

DIHYDROPYRIMIDINE DERIVATIVES

FIELD OF THE INVENTION

The present invention relatives to novel dihydropyrimidine derivatives useful as antihypertensive agents.

SUMMARY OF THE INVENTION

In accordance with the present invention novel compounds, useful for example as antihypertensive agents, are disclosed. These compounds have the general formula

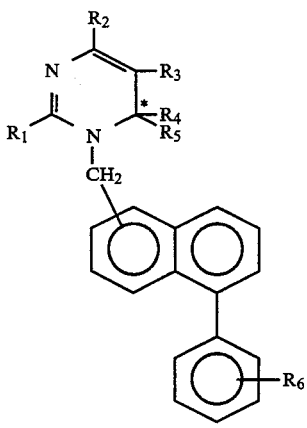

and its isomer

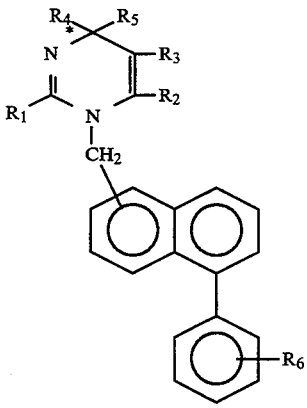

and pharmaceutically acceptable salts thereof
wherein $R_1$ is alkyl, alkenyl or alkynyl or an alkyl, alkenyl or alkynyl group substituted with F or —$CO_2R_7$; cycloalkyl; (cycloalkyl)alkyl of 4 to 10 carbon atoms; (cycloalkyl)alkenyl or (cycloalkyl)alkynyl of 5 to 10 carbon atoms; —$NR_{10}R_{11}$; —$(CH_2)_mZ(CH_2)_nR_{13}$; benzyl or benzyl substituted with 1 or 2 halogens, alkoxy of 1 to 4 carbon atoms, alkyl of 1 to 4 carbon atoms, haloalkyl or nitro; —$SR_{14}$; or —$OR_{14}$;

$R_2$ is halogen, —CN, —$OR_{14}$, —$SR_{14}$, —$COR_{14}$, $R_{15}$, ($R_{15}$O)alkyl, ($R_{15}$S)alkyl, —$CO_2R_{16}$ or (substituted amino) alkyl;

$R_3$ is —CN, —$NO_2$, 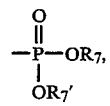

—$CONR_{10}R_{11}$, ($R_{14}OCO$)alkyl, ($R_{15}O$)alkyl, ($R_{15}S$)alkyl, ($R_{15}CO$)alkyl, —$CO_2R_{16}$, $R_{17}$, —$COR_{17}$, —$SO_2R_{17}$ or ($R_{17}OC$)alkyl;

or $R_2$ and $R_3$ taken together are

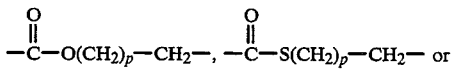

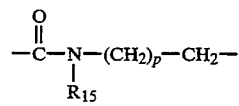

to form a 5- to 7-membered ring with the carbon atoms to which they are attached;

or $R_2$ and $R_3$ taken together with the carbon atoms to which they are attached form an aryl or heterocyclo group;

$R_4$ and $R_5$ are independently selected from hydrogen, alkyl, alkenyl, alkynyl, aryl, arylalkyl, cycloalkyl, (cycloalkyl)alkyl, heterocyclo, (heterocyclo)alkyl, haloalkyl or —$CO_2R_7$;

or $R_4$ and $R_5$ taken together with the carbon atom to which they are attached form a 5- to 7-membered carbocyclic ring which may have another 5- to 7-membered ring fused thereto;

or $R_4$ and $R_5$ together with the carbon atom to which they are attached form a carbonyl or a thiocarbonyl group;

$R_6$ is an acid moiety such as hydrogen,

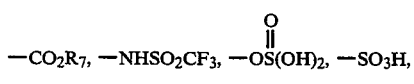

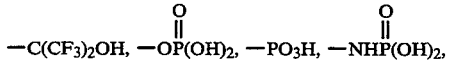

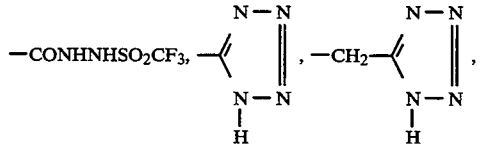

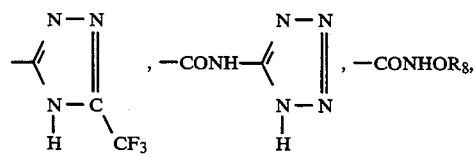

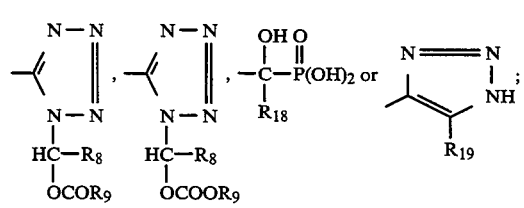

$R_7$ and $R_7'$ are independently hydrogen, alkyl, perfluoroalkyl of 1 to 8 carbon atoms, cycloalkyl of 3 to 6 carbon atoms, phenyl, benzyl,

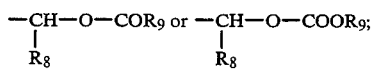

$R_8$ is hydrogen, alkyl, aryl, arylalkyl or cycloalkyl;
$R_9$ is alkyl, aryl, alkylaryl, arylalkyl or cycloalkyl;
$R_{10}$ and $R_{11}$ are independently hydrogen, alkyl of 1 to 6 carbon atoms, benzyl, α-methylbenzyl, or taken together with the nitrogen atom to which they are attached form a ring of the formula

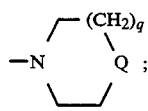

$R_{12}$ is hydrogen, alkyl of 1 to 6 carbon atoms, cycloalkyl of 3 to 6 carbon atoms, phenyl or benzyl;
$R_{13}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl groups optionally substituted with F or $-CO_2R_7$;
$R_{14}$ is alkyl, alkenyl, alkynyl, aryl, arylalkyl, cycloalkyl, (cycloalkyl)alkyl, heterocyclo, (heterocyclo)alkyl or haloalkyl;
$R_{15}$ is hydrogen, alkyl, alkenyl, alkynyl, aryl, arylalkyl, cycloalkyl, (cycloalkyl)alkyl, heterocyclo, (heterocyclo)alkyl or haloalkyl;
$R_{16}$ is hydrogen, alkyl, alkenyl, alkynyl, perfluoroalkyl of 1 to 8 carbon atoms, cycloalkyl, aryl, arylalkyl, (cycloalkyl)alkyl, heterocyclo, (heterocyclo)alkyl, haloalkyl,

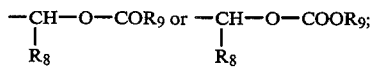

$R_{17}$ is aminoalkyl, (substituted amino)alkyl; or $R_{15}$;
$R_{18}$ is hydrogen, alkyl of 1 to 5 carbon atoms or phenyl;
$R_{19}$ is $-CN$, $-NO_2$ or $-CO_2R_7$;
Q is $-CH_2$, $-O-$, or $-NR_8$;
Z is $-O-$, $-S-$ or $-NR_{12}$;
m is an integer of 1 to 5;
n is an integer of 1 to 5;
p is 0, or the integer 1 or 2; and
q is 0, or the integer 1.

DETAILED DESCRIPTION OF THE INVENTION

The present invention relates to the compounds of formula I and I' and to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "haloalkyl" refers to such alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc., trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. The aryl group is attached by way of an available carbon atom or is fused when $R_2$ and $R_3$ taken together with the carbon atoms to which they are attached form the aryl ring. Preferred aryl groups are phenyl and monosubstituted phenyl and phenyl is most preferred.

The term "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms. The heterocyclo ring is attached by way of an available carbon atom or is fused when $R_2$ and $R_3$ taken together with the carbon atoms to which they are attached, form the heterocyclic ring. Preferred monocyclic heterocyclo groups include 2- and 3-thienyl, 2- and 3-furyl, 2-, 3- and 4-pyridyl, and imidazolyl. The heterocycle may also have a substituent selected from alkyl of 1 to 4 carbons, carboxy, alkoxy of 1 to 4 carbons and alkylthio of 1 to 4 carbons on an available carbon. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranyl. Preferred fused heterocycles include thienyl, furyl, pyridyl and imidazolyl, optionally substituted as described above.

The term "substituted amino" refers to a group of the formula $-NZ_1Z_2$ wherein $Z_1$ is hydrogen, alkyl, or aryl-$(CH_2)_p-$ and $Z_2$ is alkyl or aryl-$(CH_2)_p-$ or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

The compounds of formula I can be prepared by coupling a compound of the formula

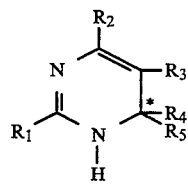

with a compound of the formula

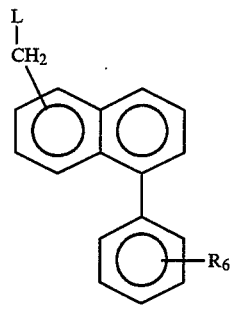

(wherein L is a leaving group, e.g., halogen,

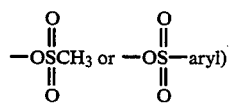

in the presence of a base, such as potassium carbonate, and in an organic solvent, such as dimethylformamide. The alkylation of compound II with compound III to give compound I is sometimes accompanied by the isomeric product I' which can be separated from product I by conventional chromatographic or crystallization techniques. When $R_4$ and $R_5$ are both alkyl groups or taken together they form a spirocarbocylic ring, I' becomes the exclusive product of alkylation. If $R_6$ contains any functional groups (e.g., carboxy, hydroxy, amino groups) that can interfere with the alkylation of II, then such groups should be protected during the reaction. Suitable protecting groups include t-butoxycarbonyl, benzyl, triphenyl methyl, etc.

A preferred method of preparing the compounds of formula I, where $R_2$ and $R_3$ together form an aryl group and $R_4$ and $R_5$ together form a carbonyl group, is by reacting compounds of formula II with a compound of the formula IIIa

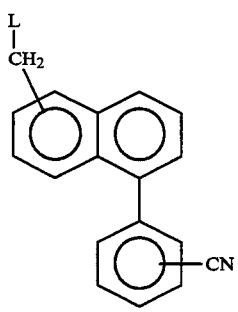

(wherein L is a leaving group, e.g., halogen,

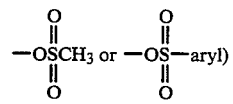

to provide compounds of formula

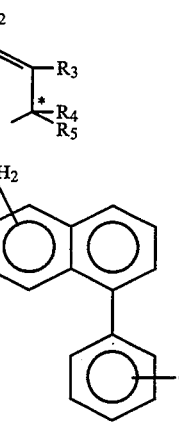

or its isomer which may then be reacted with an azide such as tributyltinazide in an organic solvent such as xylene to form compounds of formula I where $R_6$ is tetrazolyl.

Compounds of formula II wherein $R_2$ is halogen and $R_3$ is —$CO_2R_{16}$ can be prepared by first reacting an amidine of the formula

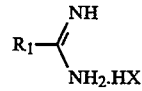

IV (wherein X is halogen) with an olefin of the formula

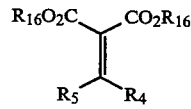

V in an organic solvent, such as dimethylformamide, and in the presence of a base, such as potassium carbonate, to provide a pyrimidine of the formula

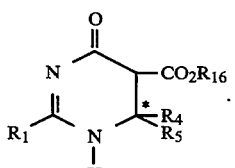

VI

The pyrimidine of formula VI can thereafter be heated in the presence of a chlorinating agent, e.g., phosphorus oxychloride to provide the intermediates of formula II were $R_2$ is chloro and $R_3$ is —$CO_2R_{16}$. Compounds of formula II where $R_2$ is a halogen other than chloro can be made in a similar fashion.

To provide the intermediates of formula II wherein $R_2$ is other than halogen, first the amidine of formula IV can be reacted with an olefin of the formula

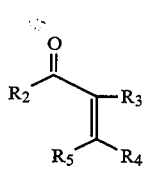

VII in the presence of a base such as sodium bicarbonate, and in an organic solvent such as dimethylformamide to provide an intermediate of the formula

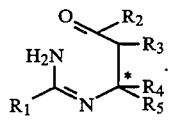

VIII

Intermediate VIII can thereafter be cyclized, e.g., by heating in the presence of an acid, such as p-toluenesulfonic acid, and in an organic solvent, such as benzene or dimethylformamide, to provide compounds of formula II where $R_2$ is other than halogen.

Compounds of formula II, wherein $R_4$ and $R_5$ together with the carbon atom to which they are attached form a carbonyl group, can be prepared by reacting a compound of the formula

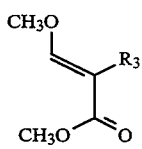

IX with an amidine of formula IV in the presence of a base such as sodium bicarbonate or sodium acetate.

Alternatively, compounds of formula II wherein $R_4$ and $R_5$ together form a carbonyl group can be prepared by reacting a compound of the formula

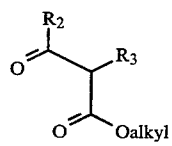

X with an amidine of formula IV in the presence of a base such as sodium bicarbonate or sodium acetate in a polar solvent such as ethanol or dimethylformamide.

Preferably, compounds of formula II wherein $R_4$ and $R_5$ together form a carbonyl group and $R_2$ and $R_3$ together form a fused aryl group, can be prepared by reacting anthranilamide with an acyl halide such as valeryl chloride ($R_1$=n—Bu) to form a compound of formula

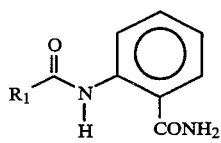

Xa

Compounds of formula Xa are then reacted in an organic solvent such as toluene with a base such as pyridine in the presence of a dehydrating agent such as molecular sieves to form the compounds of formula II.

other dihydropyrimidines of formula II can be prepared by methods described in the literature e.g., K. Atwal et al., *J. Org. Chem.*, Vol. 54, p. 5898 (1989) and references cited therein.

Compounds of formula IIIa can be prepared by reacting a compound of formula

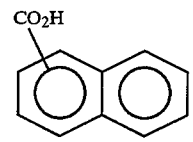

XI with a halogen (hal) to form compounds of formula

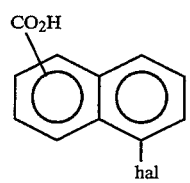

XII which are then treated with a reducing agent such as lithium aluminum hydride in an organic solvent such as ether to form compounds of formula

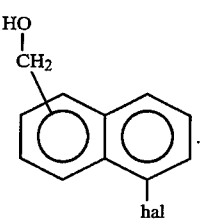

XIII

Compounds of formula XIII are then reacted with a chlorinating agent such as thionyl chloride in an organic solvent such as ether or benzene to form compounds of formula

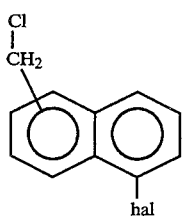

XIV which are then reacted with a metal such as zinc in an organic acid such as acetic acid to form

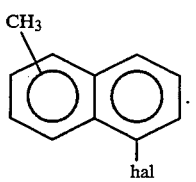

XV

Compounds of formula XV are then reacted with an alkyllithium such as butyllithium followed by a zinc salt such as zinc chloride in an organic solvent such as tetrahydrofuran to give compounds of formula

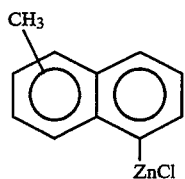

XVa which are then reacted with an aryl halide such as 2-bromobenzonitrile in the presence of a catalyst such as tetrakis (triphenylphosphine)palladium(O) to form compounds of formula

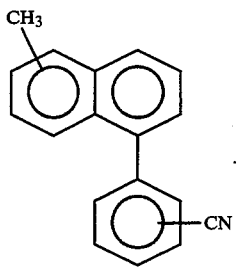

XVI

Compounds of formula XVI are then reacted with a halogenating agent such as N-bromosuccinimide to provide the compounds of formula IIIa.

The compounds of formula I and I' can have an asymmetric center within the pyrimidine ring as represented by the asterisk (*). Also, any of the R groups can have an asymmetric center. Thus, the compounds of formula I can exist in diastereomeric forms or in mixtures thereof. The above-described processes can utilize racemates, enantiomers or diastereomers as starting materials. When diastereomeric products are prepared, they can be separated by conventional chromatographic or fractional crystallization methods.

When preparing the compounds of the instant invention wherein the substituent groups contain one or more reactive functionalities such as hydroxy, amino, tetrazolyl, carboxyl, mercapto or imidazolyl groups, it may be necessary to protect these groups during the reactions in which they are used. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of the present invention are those wherein $R_1$ is alkyl of 3 to 5 carbons;

$R_2$ and $R_3$ taken together with the carbon atoms to which they are attached form a fused aryl or heterocyclic ring;

$R_4$ is hydrogen and $R_5$ is alkyl; or $R_4$ and $R_5$ together with the carbon atom to which they are attached form a carbonyl group; and $R_6$ is —$CO_2H$ or tetrazolyl;

Most preferred compounds of the present invention are those wherein $R_1$ is n-butyl;

$R_2$ and $R_3$ taken together with the carbon atoms to which they are attached form a fused benzene ring;

$R_4$ and $R_5$ together with the carbon atom to which they are attached form a carbonyl group; and $R_6$ is ortho tetrazolyl;

The present compounds of formula I and I' inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also employed. The compounds of this invention are also useful in the treatment/prevention of congestive heart failure, cardiac hypertrophy, loss of cognitive function, renal failure and are useful for kidney transplant. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension or congestive heart failure. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I and I' can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I or I' is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE

2-Butyl-3-[[5-[2-(2H-tetrazol-5-yl)phenyl]-1-naphthalenyl]methyl]-4(3H)-quinazolinone, monolithium salt A. 5-Bromo-1-naphthalenecarboxylic acid Naphthoic acid (20 g, 116 mmol) was suspended in 50 mL of acetic acid and heated to 100° C. Bromine was added dropwise over 60 minutes and the reaction became clear before a large amount of yellow solid precipitated. More acetic acid (50 mL) was added and the reaction was heated for 90 minutes at 100° C. then allowed to stand at room temperature overnight. The solid was then collected by filtration, washed with acetic acid and recrystallized from acetic acid to yield 13.42 g (46%) of the bromonaphthoic acid. M.p. 252° C.-257° C.

B. 5-Bromo-1-naphthalenemethanol

Lithium aluminum hydride (2.15 g, 56.6 mmol) was suspended in 250 mL of dry ether at 5° C. and the title A compound (13.38 g, 53.5 mmol) was added as a solid over 30 minutes. After stirring 30 minutes, the reaction was quenched with wet ether then dilute sulfuric acid. This mixture was extracted with a mixture of ethyl acetate and ether and the organic phase was washed with water, dried over magnesium sulfate and the solvent was removed to yield 9.38 g (74.5%) of a white solid.

C. 1-Bromo-5-(chloromethyl)naphthalene

The title B compound (9.18 g, 38.9 mmol) was suspended in 92 mL of ether and 18 mL of benzene. Thionyl chloride (3.9 mL, 53.5 mmol) was added and the mixture was stirred at room temperature for seven hours. The mixture was stored at −15° C. for 2.5 days then warmed to room temperature and additonal thionyl chloride (0.5 mL, 6.9 mmol) was added. The reaction was stirred for 24 hours at room temperature then filtered and the solvent removed to provide 8 g of a solid which was adsorbed onto silica gel and purified by flash chromatography (160 g silica gel;hexane) to yield 4.74 g (48%) of a white solid.

D. 1-Bromo-5-methylnaphthalene

Powdered zinc (4.24 g, 64.9 mmol) was suspended in ether (20 mL) and acetic acid (12 mL, 210 mmol) was added. The title C compound (4.48 g, 17.5 mmol) was dissolved in ether (60 mL) and added dropwise over five minutes. After stirring for 2.5 hours the reaction was complete (aliquot analyzed by NMR) and the ether was removed. The residue was partitioned between ethyl acetate and water and the aqueous layer extracted with ethyl acetate. The organic phase was dried over magnesium sulfate, filtered and the solvent removed to provide 3.52 g of a tan solid. Purification by flash chromatography (140 g silica gel;hexane) yielded 3.11 g (80%) of a white solid. M.p. 53° C.-56° C.

E. 2-(5-Methyl-1-naphthalenyl)benzonitrile

The title D compound (1.99 g, 9.00 mmol) was dissolved in 10 mL of freshly distilled tetrahydrofuran, cooled to −78° C. and n-butyllithium (2.23M in hexane, 4.24 mL, 9.45 mmol) was added dropwise over 10 minutes. Upon complete addition the reaction was cloudy, bright yellow. After stirring 40 minutes, zinc chloride (1.0M in ether, 9.45 mL, 9.45 mmol) was added and the reaction mixture turned to clear pale yellow. The reaction was stirred 30 minutes, then the cold bath was removed and the reaction stirred an additional 30 minutes before 2-bromobenzonitrile (1.64 g, 9.45 mmol) and tetrakis(triphenylphosphine)palladium(O) (520 mg, 0.45 mmol) were added. After stirring 22 hours at 55° C., the reaction mixture was adsorbed on 10 g of silica gel and purified by flash chromatography (170 g silica gel; 30% toluene, hexane) to yield 1.31 g (60%) of the product as a white solid.

F. 2-[5-(Bromomethyl)-1-naphthalenyl]-benzonitrile

The title E compound (1.13 g, 4.64 mmol) was dissolved in 28 mL of 50% benzene in carbontetrachloride. Azobisisobutyrylnitrile (76 mg, 0.46 mmol) was added and the mixture was irradiated for 1.5 hours with a 300 w incandescent light bulb. The solvent was removed and the residue adsorbed onto 10 g of silica gel and purified by flash chromatography (150 g silica gel; 10% ethyl acetate, hexane) to yield 1.56 g (100%) of a white solid. M.p. 147° C.-149° C.

G. 2-Butyl-4(3H)-quinazolinone 1. 2-[(1-Oxopentyl)amino]benzamide

Valeryl chloride (6.0 mL, 50 mmol) was added to a mixture of anthranilamide (6.8 g, 50 mmol) and triethylamine (7.0 mL, 50 mmol) in tetrahydrofuran (100 mL) at 25° C. A rapid, exothermic reaction was observed, but no external cooling was required to prevent reflux. The mixture was stirred at ambient temperature for 19 hours, after which it was poured into excess aqueous sodium bicarbonate solution, extracted with ethyl acetate, dried (magnesium sulfate), and concentrated in vacuo. The residue was triturated with hexane/ether to give the title compound as a tan solid (9.9 g, 90%); M.p. 119° C.-120° C.

2. 2-Butyl-4(3H)-quinazolinone

A mixture of the title 1 compound (9.2 g, 42 mmol), toluene (200 mL) and pyridine (150 mL) was heated to reflux, after which molecular sieves (3 Å 100 mL) were added. The mixture was heated at reflux for two hours, more molecular sieves (100 mL) were added and reflux was continued for a total of 18 hours. The mixture was then filtered and the filtrate was concentrated in vacuo. The residue was dissolved in chloroform (500 mL), filtered again (millipore), and reconcentrated. The residue was triturated with hexanes to give the title compound as a white solid (6.8 g, 80%); M.p. 153° C.-155° C.

H. 2-Butyl-3-[[5-(2-cyanophenyl) -1-naphthalenyl]methyl]-4(3H)-quinazolinone

The title F compound (500 mg, 1.55 mmol), the title G compound (345 mg, 1.71 mmol) and potassium carbonate (ground, 279 mg, 2.02 mmol) were dissolved in 3.2 mL of N,N-dimethylformamide. The mixture was stirred for 18 hours then filtered through celite, adsorbed onto 5 g of silica gel and purified by flash chromatography (100 g silica gel; 20% ethyl acetate, hexane) to yield 162 mg (23%) of the O-alkylated product and 270 mg (39%) of the desired product as a white solid. M.p. 92° C.-95° C.;

Anal. calc'd for $C_{30}H_{25}N_3O.0.24$ water: C, 80.46; H, 5.73; N, 9.38. Found: C, 80.41; H, 5.49; N, 9.43.

I. 2-Butyl-3-[[5-[2-(2H-tetrazol-5-yl)phenyl]-1-naphthalenyl]methyl]-4(3H)-quinazolinone, monolithium salt The title H compound (260 mg, 0.59 mmol) was suspended in 1 mL of xylene. Tributyltin azide (520 μL) was added and the mixture heated for 20 hours at 100° C. Additional tributyltin azide (200 μL) was added and the mixture was again heated for 12 hours at 100° C. The reaction mixture was cooled and purified by flash chromatography (90 g silica gel; 5% acetic acid, 35% ethyl acetate, hexane) to yield 266 mg of the desired product as a foamy yellow oil. This oil was dissolved in 1.2 mL of 1.0N lithium hydroxide and purified by column chromatography (100 mL HP-20; eluting with acetone-water) to yield 211 mg (75%) of the desired product as the lithium salt. M.p. >270° C.

Anal. calc'd for $C_{30}H_{25}N_6O \cdot 1.70$ water: C, 68.88; H, 5.47; N, 16.06. Found C, 69.23; H, 5.43; N, 15.71.

What is claimed is:

1. A compound of the formula I

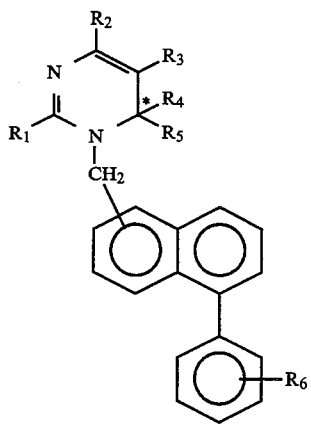

or its isomer

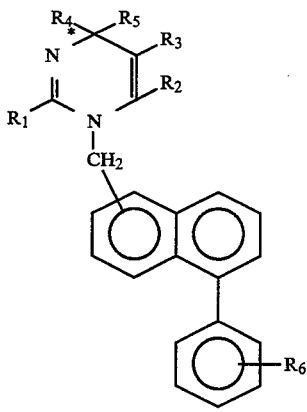

or a pharmaceutically acceptable salt thereof
wherein $R_1$ is alkyl, alkenyl or alkynyl or an alkyl, alkenyl or alkynyl group substituted with F or —$CO_2R_7$; cycloalkyl; (cycloalkyl)alkyl of 4 to 10 carbon atoms; (cycloalkyl)alkenyl or (cycloalkyl)alkynyl of 5 to 10 carbon atoms; —$NR_{10}R_{11}$; —$(CH_2)_mZ(CH_2)_mR_{13}$; benzyl or benzyl substituted with 1 or 2 halogens, alkoxy of 1 to 4 carbon atoms, alkyl of 1 to 4 carbon atoms, haloalkyl or nitro; —$SR_{14}$; or —$OR_{14}$;

$R_2$ and $R_3$ taken together with the carbon atoms to which they are attached form an aryl group;

$R_4$ and $R_5$ are independently selected from hydrogen, alkyl, alkenyl, alkynyl, aryl, arylalkyl, cycloalkyl, (cycloalkyl)alkyl, heterocyclo, (heterocyclo)alkyl, haloalkyl or —$CO_2R_7$;

or $R_4$ and $R_5$ taken together with the carbon atom to which they are attached form a 5- to 7-membered carbocyclic ring which may have another 5- to 7-membered ring fused thereto;

or $R_4$ and $R_5$ taken together with the carbon atom to which they are attached form a carbonyl or a thiocarbonyl group;

$R_6$ is an acid moiety such as hydrogen,

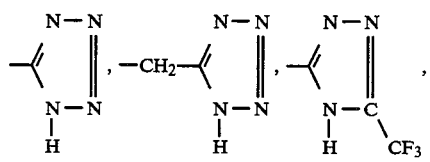

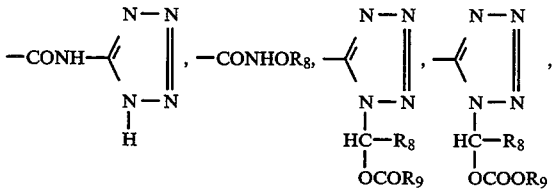

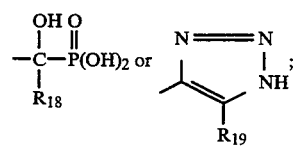

$R_7$ is hydrogen, alkyl, perfluoroalkyl of 1 to 8 carbon atoms, cycloalkyl of 3 to 6 carbon atoms, phenyl, benzyl

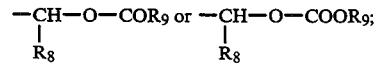

$R_8$ is hydrogen, alkyl, aryl, arylalkyl or cycloalkyl;
$R_9$ is alkyl, aryl, alkylaryl, arylalkyl or cycloalkyl;
$R_{10}$ and $R_{11}$ are independently hydrogen, alkyl of 1 to 6 carbon atoms, benzyl, α-methylbenzyl, or taken together with the nitrogen atom to which they are attached form a ring of the formula

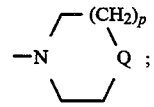

$R_{12}$ is hydrogen, alkyl of 1 to 6 carbon atoms, cycloalkyl of 3 to 6 carbon atoms, phenyl or benzyl;
$R_{13}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl groups optionally substituted with F or —$CO_2R_7$;
$R_{14}$ is alkyl, alkenyl, alkynyl, aryl, arylalkyl, cycloalkyl, (cycloalkyl)alkyl, heterocyclo, (heterocyclo)alkyl or haloalkyl;
$R_{18}$ is hydrogen, alkyl of 1 to 5 carbon atoms or phenyl;
$R_{19}$ is —CN, —$NO_2$ or —$CO_2R_7$;
Q is —$CH_2$, —O—, or —$NR_8$;
Z is —O—, —S— or —$NR_{12}$;
m is an integer of 1 to 5; and p is 0, or the integer 1 or 2.

2. A compound of claim 1 wherein $R_1$ is n-butyl;

$R_2$ and $R_3$ taken together with the carbon atoms to which they are attached from a fused benzene ring;

$R_4$ and $R_5$ together with the carbon atom to which they are attached form a carbonyl group; and $R_6$ is ortho tetrazolyl.

3. A compound of claim 1 having the name 2-Butyl-3-[[5-[2-(2H-tetrazol-5-yl)phenyl]-1-naphthalenyl]methyl]-4(3H)-quinazolinone, or a pharmaceutically acceptable salt thereof.

4. A pharmaceutical composition comprising a compound of claim 1 and a pharmaceutically acceptable carrier.

5. A method for treating hypertension comprising administering to a mammalian specie in need thereof a therapeutically effective amount of a composition of claim 4.

6. A method for treating congestive heart failure comprising administering to a mammalian specie in need thereof a therapeutically effective amount of a composition of claim 4.

7. A method for preventing cardiac hypertrophy comprising administering to a mammalian specie in need thereof a therapeutically effective amount of a composition of claim 4.

* * * * *